United States Patent [19]

Buathier et al.

[11] 4,334,083
[45] Jun. 8, 1982

[54] PROCESS FOR THE PREPARATION OF AN ALKYL 2-CHLOROPROPIONATE BY CHLORINATING AN ALKYL LACTATE

[75] Inventors: Bernard Buathier, St. Cyr au Mont d'Or; André Bernard, Villeurbanne, both of France

[73] Assignee: Rhone-Poulenc Agrochimie, Lyons, France

[21] Appl. No.: 152,098

[22] Filed: May 21, 1980

[30] Foreign Application Priority Data

Jun. 20, 1979 [FR] France ................................ 79 16335

[51] Int. Cl.$^3$ .............................................. C07C 69/63
[52] U.S. Cl. ..................................... 560/226; 560/150
[58] Field of Search ......................................... 560/226

[56] References Cited

FOREIGN PATENT DOCUMENTS 1479271 3/1967 France .

OTHER PUBLICATIONS

Darzens, Comptes Rendus Hebdomadaires des Séances de l'Academie des Sciences, 152, 1314–1317 and 1601–1603, (1911).
Frankland et al., J. Chem. Soc. 105, 1101–1115, (1914).

Weygand, *Preparative Organic Chemistry*, pp. 222–223, (1972).
Fieser et al., *Reagents for Organic Synthesis*, vol. 1, pp. 1160–1161, (1967).

*Primary Examiner*—Paul J. Killos
*Attorney, Agent, or Firm*—Browdy and Neimark

[57] ABSTRACT

A racemic or optically active alkyl 2-chloropropionate is prepared, respectively, from a racemic or optically active alkyl lactate by, in a first step, gradually bringing the alkyl lactate into contact with the thionyl chloride, in the presence of an organic base, while maintaining, in the reaction mixture, an excess of thionyl chloride, relative to the amount of alkyl lactate introduced into this mixture, at a temperature below the decomposition point of the chlorosulphinate of the alkyl lactate, which is formed as an intermediate, and then, in a second step, in heating the reaction mixture resulting from the first step at a temperature which is at least equal to the decomposition point of the chlorosulphinate of the alkyl lactate.

The alkyl 2-chloropropionates can be used for the manufacture of the racemic or optically active 2-phenoxypropionic acids.

9 Claims, No Drawings

PROCESS FOR THE PREPARATION OF AN ALKYL 2-CHLOROPROPIONATE BY CHLORINATING AN ALKYL LACTATE

The invention relates to the preparation of an alkyl 2-chloropropionate of the formula:

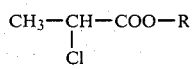  (formula I)

in which R represents an alkyl radical containing from 1 to 5 carbon atoms, by chlorinating an alkyl lactate of the formula:

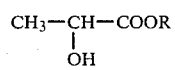  (formula II)

in which R has the same meaning as above.

The compound of the formula I and the compound of the formula II possess an asymmetrically substituted carbon atom. Each of these compounds can therefore exist in two enantiomeric forms, one of which possesses the D absolute configuration and the other of which possesses the L absolute configuration. (According to another nomenclature, which is equivalent, the letters R and S are sometimes used instead of D and L, respectively, in order to identify the absolute configurations. In the following text, the first of these nomenclatures, i.e. the letters D and L, will be used systematically). II) which comprises equal proportions by weight of the isomer of the D absolute configuration and the isomer of the L absolute configuration is the optically inactive, racemic compound.

In the following text, the term optically active compound is to be understood as meaning a compound which predominantly (by weight) or totally comprises one of the isomers of this compound. The term optical purity of an optically active compound, i.e. a compound which predomantly consists of one of the two isomers, is to be understood as meaning the percentage by weight of the preponderant isomer present in this compound. The term optically active compound of high optical purity is to be understood as meaning a compound in which the percentage by weight of the preponderant isomer is at least 90%.

The invention relates to the preparation of a racemic or optically active alkyl 2-chloropropionate corresponding to the formula I. More particularly, it relates to the preparation of an optically active alkyl 2-chloropropionate having a high optical purity.

It is known from the reference J. Chem. Soc. 105 1101–15 to prepare optically active ethyl 2-chloropropionate by chlorinating optically active ethyl lactate in accordance with a process comprising the following two separate successive steps:

First step:
The reaction of thionyl chloride with ethyl lactate (dextrorotatory, measurement carried out without a solvent) to give the chlorosulphinate of ethyl lactate in accordance with the equation:

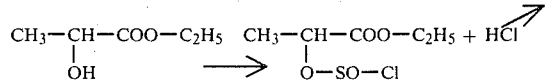

According to this reference, this reaction is carried out using a large excess of thionyl chloride (50% molar excess, relative to the ethyl lactate, according to the experiment described). The reaction already starts at ordinary temperature and involves vigorous evolution of hydrogen chloride.

Second step:
The thermal decomposition of the chlorosulphinate of ethyl lactate, obtained above, by heating the latter, in the presence of pyridine hydrochloride as a catalyst, to give ethyl 2-chloropropionate in accordance with the equation:

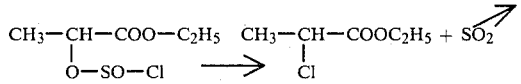

According to the experiment described on page 1,113 of this reference, this thermal decomposition is carried out by heating the chlorosulphinate of ethyl lactate at 80° C. for six hours, in the presence of pyridine hydrochloride in an amount which represents approximately 23% by weight, relative to the chlorosulphinate of ethyl lactate.

However, this reference teaches that this preparation presents a certain number of difficulties:

Firstly, it points out that, during the first step of the process, there is vigorous evolution of HCl (compare page 1,112), even when this first step is carried out at ordinary temperature. This violent evolution of gas is not too troublesome in the case of a laboratory experiment, but the situation is quite different if it is envisaged to carry out such a process on an industrial scale, because this violent evolution of gas then becomes unacceptable.

This reference further points out that there are side reactions leading to the formation of undesirable by-products, and this very obviously reduces the formation of ethyl 2-chloropropionate (and hence the yield of this compound) accordingly. It also points out that, depending on the conditions chosen, the use of pyridine hydrochloride as a catalyst causes a certain partial racemisation of the ethyl 2-chloropropionate (compare pages 1,106–1,114). It will be noted in this respect that the object of the experiment described in this reference was not to obtain optically pure ethyl L-2-chloropropionate, but simply to determine the direction of the optical rotation of the ethyl 2-chloropropionate obtained, in order to study the stereochemistry of the reaction. This partial racemisation is not troublesome in the case of a theoretical study such as that described in this reference, but the situation is quite different when an attempt is made to prepare an optically active alkyl 2-chloropropionate, of high optical purity, from an optically active alkyl lactate, which is itself of high optical purity, because this partial racemisation during the reaction causes a reduction in the optical purity during the reaction and can lead to an alkyl 2-chloropropionate having a high degree of racemisation.

The present invention proposes to overcome these disadvantages.

A first object of the invention is to make it possible to prepare a racemic or optically active alkyl 2-chloropropionate by reacting excess thionyl chloride with a racemic or optically active alkyl lactate, with the intermediate formation of the chlorosulphinate of the alkyl lactate, the evolution of hydrogen chloride during the reaction being spread over the maximum possible time in order to bring it down to an industrially acceptable level.

A second object of the invention is to make it possible to prepare a racemic or optically active alkyl 2-chloropropionate from an alkyl lactate which is respectively either racemic or optically active, with an improved yield and whilst avoiding the formation of troublesome by-products.

A third object is to make it possible to prepare an optically active alkyl 2-chloropropionate from an optically active alkyl lactate whilst avoiding, to the maximum extent, any phenomenon of partial racemisation during the conversion, and thus to make it possible to obtain an alkyl 2-chloropropionate of high optical purity from an alkyl lactate of high optical purity.

It has now been found that these various objects can be achieved by virtue of a new process forming the subject of the present invention.

The process according to the invention relates to the preparation of the racemic or optically active alkyl 2-chloropropionate of the formula I, by reacting excess thionyl chloride with the racemic or optically active alkyl lactate of the formula II, with, in a first step, the formation of the chlorosulphinate of the alkyl lactate, and then, in a second step, the thermal decomposition of the chlorosulphinate of the alkyl lactate, which process comprises, during the first step, gradually bringing the alkyl lactate into contact with the thionyl chloride, in the presence of an organic base (e.g. pyridine, quinoline or dimethylformamide), whilst maintaining, in the reaction mixture, a molar excess of thionyl chloride of at least 2.5%, relative to the amount of alkyl lactate introduced into this mixture, at a temperature which is kept below the decomposition point of the chlorosulphinate of the alkyl lactate throughout this first step, and, in the second step, heating the reaction mixture resulting from the first step at a temperature which is at least equal to the decomposition point of the chlorosulphinate of the alkyl lactate.

Advantageously, the conditions used for carrying out the process according to the invention are as follows, it being possible for these conditions to be considered in isolation or taken in combination with one another:

a. During the first step of the process, the alkyl lactate is gradually brought into contact with the thionyl chloride by gradually running the alkyl lactate into the reaction mixture containing at least some of the thionyl chloride and at least some of the organic base. In order to do this, according to a preferred embodiment of the invention, all the organic base and all the thionyl chloride are placed in the reactor used and the alkyl lactate is gradually run into this mixture, this rate of introduction being adjusted according to the evolution of gas. According to another preferred embodiment of the process according to the invention, the organic base and some of the thionyl chloride are placed in the reactor and the alkyl lactate and the remainder of the thionyl chloride are simultaneously run into this mixture, the respective rates of introduction of the reactants being adjusted so that, throughout this first step, the reaction mixture contains a molar excess of thionyl chloride of at least 2.5%, relative to the alkyl lactate introduced, and so that the evolution of hydrogen chloride remains at an industrially acceptable level. Advantageously, the hydrogen chloride evolved is absorbed by a scrubbing column, the hourly absorption capacity of which is known. It is understood that, because the reaction of the alkyl lactate with the thionyl chloride is virtually instantaneous, it is possible to adjust the rates of introduction of the alkyl lactate and, if appropriate, of the thionyl chloride so that the volume of hydrogen chloride evolved per hour remains within the hourly absorption capacity of the scrubbing column.

b. Preferably, pyridine is used as the organic base in an amount which is equal to at least 0.05% by weight, relative to the amount of alkyl lactate to be converted. The upper limit to this amount is not critical in the case where the process according to the invention involves the preparation of a racemic alkyl 2-chloropropionate or the preparation of an optically active alkyl 2-chloropropionate for which a drop in optical purity, resulting from partial racemisation during the reaction, is acceptable; however, for economic reasons, it is advantageous not to use more than 10% by weight of pyridine, relative to the amount of alkyl lactate to be converted.

In the case where the process according to the invention is applied to the preparation of an optically active alkyl 2-chloropropionate, and where it is desired to avoid, to the maximum extent, any phenomenon of partial racemisation during the reaction, the amount of pyridine used is also between 0.05% and 2% by weight, relative to the amount of alkyl lactate to be converted, and preferably between 0.1% and 1% by weight.

The pyridine can be introduced into the reaction mixture gradually throughout the first step, or at the end of the first step, but it is preferably introduced at the start of the first step of the process.

c. During the first step of the process, the temperature of the reaction mixture is between 0° and 70° C. and preferably between 15° and 65° C.

d. The time required to bring all the thionyl chloride into contact with all the alkyl lactate is at least 2 hours and preferably between 3 and 5 hours, and the alkyl lactate is run in at a constant rate throughout the first step.

e. In total, the molar excess of thionyl chloride used is at least 2.5%, relative to the alkyl lactate to be converted, and preferably between 5 and 25%.

f. During the second step of the process, the reaction mixture is heated at a temperature between 60° C. and 120° C. until all evolution of gas has ceased. However, in the case where the process according to the invention is applied to the preparation of an optically active alkyl 2-chloropropionate, and where it is desired to avoid, to the maximum extent, any partial racemisation during the reaction, this temperature must not exceed 80° C.

During the second step of the process, it is also possible to restrict the evolution of gas to an industrially acceptable level by gradually increasing the temperature at which the reaction mixture is heated, and, if necessary, by creating periods during which the temperature is kept constant. Advantageously, the duration of the second step of the process is at least one hour and preferably between 2 and 10 hours. The $SO_2$ evolved during the second step can be absorbed in a scrubbing column.

At the end of the second step, the crude alkyl 2-chloropropionate obtained can be purified by the customary methods, in particular by distillation and/or alkaline scrubbing.

The process according to the invention can be used for the preparation of racemic alkyl 2-chloropropionates from racemic alkyl lactates.

The racemic alkyl 2-chloropropionates thus obtained can be used, after saponification, for the preparation of 2-phenoxypropionic acid derivatives known for their herbicidal and phytohormonal properties, such as 2-(2-methyl-4-chlorophenoxy)-propionic acid (or MCPP), 2-(2,4-dichlorophenoxy)-propionic acid (or 2,4-DP), 2-(2,4,5-trichlorophenoxy)-propionic acid (or 2,4,5-TP) and 2-(2-methylphenoxy)-propionic acid (or MPP).

Preferably, the process according to the invention involves the preparation of optically active alkyl 2-chloropropionates, which predominantly or totally comprise one of the optical isomers, from alkyl lactates which are themselves optically active, the conversion of the alkyl lactate to the alkyl 2-chloropropionate taking place with an inversion of configuration of the Walden inversion type.

The process makes it possible, in particular, to prepare alkyl L-2-chloropropionates from the corresponding alkyl D-lactates and also to prepare alkyl D-2-chloropropionates from the corresponding alkyl L-lactates.

The alkyl L-2-chloropropionates obtained according to the invention can advantageously be used as the starting material for the preparation of D-2-phenoxypropionic acids in accordance with the process described in French Pat. No. 1,479,271.

The following examples illustrate the invention without however limiting it. It will be observed that, for each of these examples, the yield of alkyl 2-chloropropionate is very high and frequently more than 95%. It will also be observed that, for all the examples described below, the reaction is carried out without using a solvent. However, if desired, this reaction can be carried out in a solvent medium, provided, however, that the solvent used does not change the stereochemistry of the reaction. Dioxane may be mentioned as an example of a solvent which can be used.

EXAMPLE 1

A round-bottomed flask is used which is equipped with a stirrer, a Vigreux-type condenser, a thermometer, a dropping funnel and liquid nitrogen traps arranged downstream of the condenser.

Methyl lactate (832 g, 8 mols), $[\alpha]_D^{20} = +7.48°$ (without a solvent), is placed in the dropping funnel and thionyl chloride (1,060 g, 8.9 mols) and pyridine (4.15 g, i.e. 0.49% by weight of the amount of methyl lactate to be converted) are placed in the flask.

The methyl lactate contains about 1.03% of ethyl lactate as an impurity and 0.61% of other impurities including methyl lactyllactate.

The temperature of the flask is raised to 60° C., whilst stirring, and the methyl lactate is run in over a period of 4 hours, whilst keeping this temperature constant. When the introduction is complete, the temperature is raised to 75° C. and this temperature is maintained for 1 hour. Analysis by gas phase chromatography, carried out at this moment, shows that there is no more methyl lactate in the reaction mixture. Heating is continued for 20 minutes and the mixture is then left to cool for 20 minutes, under a partial vacuum of about 150 mm Hg, to a temperature of about 40°-45° C.

A crude product (992.5 g. 884 ml), comprising crude methyl 2-chloropropionate, $SO_2$ (19.2 g), $SOCl_2$ (1.6 g) and HCl (1.8 g), is obtained.

Analysis, by gas phase chromatography, of the crude methyl 2-chloropropionate thus obtained gives the following composition by weight (excluding $SO_2$, $SOCl_2$, HCl and pyridine):

| | |
|---|---|
| methyl 2-chloropropionate | 97.7% |
| ethyl chloropropionate | 1.22% |
| methyl acetyllactate | 0.04% |
| methyl acetyllactyllactate | 0.08% |
| chloropropionate of methyl lactate | 0.67% |
| chloropropionate of ethyl lactate | 0.01% |
| lactide (cyclised methyl lactate) | 0.03% |
| chloropropionate of methyl lactyllactate | 0.11% |
| unidentified impurities | 0.14% |

The formation of ethyl chloropropionate, methyl acetyllactate and methyl acetyllactyllactate results from the impurities present in the starting methyl lactate (yield of methyl 2-chloropropionate: 98%).

The crude product obtained above (900 g) is distilled, under a pressure of 20 mm Hg, in a 40 cm high packed column. When distillation is complete, the vacuum is increased to 3 mm Hg. At the outlet of the packed column, the uncondensed vapours pass into a liquid nitrogen trap.

Distillation makes it possible to obtain the following three fractions:

methyl 2-chloropropionate (95 g) of optical rotation $[\alpha]_D^{20} = -25.37°$ (without a solvent), methyl 2-chloropropionate (675 g) of optical rotation $[\alpha]_D^{20} = -25.26°$ (without a solvent), and methyl 2-chloropropionate (71 g) of optical rotation $[\alpha]_D^{20} = -24.56°$ (without a solvent).

At the bottom of the column, a residue (13 g) consisting of heavy products is recovered.

In the liquid nitrogen trap, methyl 2-chloropropionate (17 g) containing traces of HCl, $SO_2$ and $SOCl_2$ is recovered.

After distillation, and taking account of the 2-chloropropionate recovered in the nitrogen trap, the yield is 97.2%.

According to the literature (Beilstein E 3, page 553), methyl L-2-chloropropionate has an optical rotation $[\alpha]_D^{20} = -27.8°$ (without a solvent). In view of this fact, the optical purity of the 2-chloropropionate obtained in the second distillation fraction is 95.4% (i.e. the compound obtained contains 95.4% of the L isomer and 4.6% of the D isomer).

According to the literature (Beilstein E 3, page 449), methyl D-lactate has an optical rotation $[\alpha]_D^{19} = +8.2°$ (without a solvent); in view of this fact, the optical purity of the starting methyl lactate was 95.6%. It is thus observed that the conversion of the methyl lactate to the methyl 2-chloropropionate did not cause substantial racemisation.

EXAMPLE 2

The method described in Example 1 is followed, using methyl lactate (832 g, 8 mols) of the same optical rotation as in Example 1, thionyl chloride (1,070 g, 8.99 mols) and pyridine (2.1 g).

The methyl lactate is run in at 60° C. in the course of 4 hours and this is followed by heating at 75° C. for 1 hour 30 minutes.

After cooling in a partial vacuum, a crude product (906.5 ml, i.e. 1,020 g), containing crude methyl 2-chloropropionate, SO$_2$ (42.9 g), SOCl$_2$ (14.42 g) and HCl (0.75 g), is recovered.

Analysis, by gas phase chromatography, of the crude methyl 2-chloropropionate obtained gives the following composition by weight:

| | |
|---|---|
| methyl 2-chloropropionate | 97.49% |
| ethyl chloropropionate | 1.26% |
| methyl acetyllactate | 0.04% |
| methyl acetyllactyllactate | 0.09% |
| chloropropionate of methyl lactate | 0.80% |
| chloropropionate of ethyl lactate | 0.01% |
| lactide (cyclised methyl lactate) | 0.04% |
| chloropropionate of methyl lactyllactate | 0.14% |
| unidentified impurities | 0.13% |

Distillation of the crude methyl 2-chloropropionate obtained above (900 g) gives the following fractions:

top fraction: 98 g $[\alpha]_D^{20} = -25.10°$ (without a solvent)

middle fraction: 663 g $[\alpha]_D^{20} = -25.36°$ (without a solvent)

bottom fraction: 55 g $[\alpha]_D^{20} = -25.00°$ (without a solvent).

At the bottom of the column, a residue (8.5 g) consisting of heavy products is collected.

In the liquid nitrogen trap, methyl 2-chloropropionate (37 g) containing traces of HCl, SO$_2$ and SOCl$_2$ is recovered.

After distillation, and taking account of the product recovered in the nitrogen trap, the yield of methyl chloropropionate is 98.6%. The optical purity, calculated for the middle fraction, is 95.6%.

EXAMPLE 3

The method described in Example 1 is followed, using methyl lactate (832 g, 8 mols) of the same optical rotation as in Example 1, thionyl chloride (1,070 g, 8.99 mols) and pyridine (1 g).

The methyl lactate is run in at 60° C. in the course of 4 hours and this is followed by heating at 75° C. for 2 hours.

After cooling in a partial vacuum, a crude product (1,026 g, i.e. 910 ml), containing crude methyl 2-chloropropionate, SO$_2$ (42.5 g) and SOCl$_2$ (22.8 g), is recovered.

In the liquid nitrogen traps, methyl 2-chloropropionate (44.5 ml, i.e. 70 g), containing SO$_2$ (11.3 g), HCl (12.9 g, i.e. 291.67 g/liter) and thionyl chloride (40.0 g), is recovered.

Analysis, by gas phase chromatography, of the crude methyl 2-chloropropionate obtained gives the following composition by weight:

| | |
|---|---|
| methyl 2-chloropropionate | 97.53% |
| ethyl chloropropionate | 1.15% |
| methyl acetyllactate | 0.04% |
| methyl acetyllactyllactate | 0.08% |
| chloropropionate of methyl lactate | 0.67% |
| chloropropionate of ethyl lactate | 0.01% |
| lactide (cyclised methyl lactate) | 0.04% |
| chloropropionate of methyl lactyllactate | 0.34% |
| unidentified impurities | 0.14% |

Distillation of the crude methyl chloropropionate obtained above (900 g) gives the following fractions:

top fraction: 99 g $[\alpha]_D^{20} = -25.29°$ without a solvent middle fraction: 652 g $[\alpha]_D^{20} = -25.34°$ without a solvent bottom fraction: 58 g $[\alpha]_D^{20} = -24.97°$ without a solvent.

At the bottom of the column, a residue (9 g) consisting of heavy products is collected.

In the liquid nitrogen trap, methyl 2-chloropropionate (29 g) is recovered.

After distillation, and taking account of the product recovered in the traps, the yield of methyl 2-chloropropionate is 98.2%.

The optical purity of the methyl 2-chloropropionate originating from distillation (middle fraction) is 95.5%.

EXAMPLE 4

The device used is the same as in Example 1 except that the Vigreux-type condenser is replaced by a brine condenser. The method described in Example 1 is followed, using ethyl lactate (590 g, 5 mols) of optical rotation $[\alpha]_D^{20} = -10.65°$ (without a solvent), thionyl chloride (640 g, 5.37 mols) and pyridine (1.2 g).

The ethyl lactate is run in at 60° C. in the course of 4 hours and this is followed by heating at 75° C. for 1 hour 45 minutes. After cooling under atmospheric pressure, a crude product (713 g) consisting mainly of ethyl 2-chloropropionate is recovered.

Distillation of an aliquot part of this product under a pressure of 15 mm Hg (T: 50°–52° C.) makes it possible to recover a fraction of optical rotation $[\alpha]_D^{20} = +19.33°$ (without a solvent), which is composed of at least 99.9% of ethyl 2-chloropropionate, and a residue which represents 5.5% by weight of the amount of product subjected to distillation and is composed of 60% by weight of ethyl 2-chloropropionate and 40% by weight of heavy products.

The yield of ethyl 2-chloropropionate (taking account of the ethyl chloropropionate in the heavy products) is 97%.

EXAMPLE 5

The procedure of Example 4 is followed, using isopropyl lactate (660 g, 5 mols) of optical rotation $[\alpha]_D^{20} = -10.75°$ (without a solvent), thionyl chloride (640 g, 5.37 mols) and pyridine (1.2 g).

The isopropyl lactate is run in at 60° C. in the course of 4 hours and this is followed by heating at 75° C. for 1 hour 35 minutes.

After cooling under atmospheric pressure, a crude product (825 g) consisting mainly of crude isopropyl 2-chloropropionate is recovered.

Distillation of the crude product obtained above (750 g) under a pressure of 10 mm Hg (T: 50°–52° C.) makes it possible to recover a first fraction (114 g) of optical rotation $[\alpha]_D^{20} = +13.42°$ (without a solvent), which is composed of at least 90% by weight of isopropyl 2-chloropropionate and contains 8.84% of thionyl chloride and 0.2% of free SO$_2$, a second fraction (488 g) of optical rotation $[\alpha]_D^{20} = +14.02°$ (without a solvent), which is composed of at least 99.5% by weight of isopropyl 2-chloropropionate and contains less than 0.1% by weight of thionyl chloride and less than 0.1% by weight of SO$_2$, and a residue (60 g) which is composed of 81% of isopropyl 2-chloropropionate and 19% of heavy products.

The yield of isopropyl 2-chloropropionate is 95.7%.

EXAMPLE 6

The procedure of Example 5 is followed, using n-butyl lactate (584 g, 4 mols) of optical rotation $[\alpha]_D^{20} = -2.77°$ (without a solvent), thionyl chloride (512 g, 4.30 mols) and pyridine (1.2 g).

The n-butyl lactate is run in at 60° C. in the course of 4 hours and this is followed by heating at 75° C. for 1 hour 15 minutes. After cooling under atmospheric pressure, a crude product (690 g) composed mainly of n-butyl 2-chloropropionate is recovered.

Distillation of the crude product obtained (600 g) under a pressure of 1 mm Hg (T: 66°–69° C.) gives a first fraction (127 g) of optical rotation $[\alpha]_D^{20} = +2.77°$ (without a solvent), which is composed of at least 99% by weight of n-butyl 2-chloropropionate and contains 0.16% by weight of free $SO_2$ and less than 0.1% of thionyl chloride, a second fraction (371 g) of optical rotation $[\alpha]_D^{20} = +2.75°$ (without a solvent), which is composed of at least 99.5% by weight of n-butyl 2-chloropropionate and contains less than 0.1% of free $SO_2$ and less than 0.1% of thionyl chloride, and a residue (33 g) which is composed of 97% by weight of n-butyl 2-chloropropionate and 3% of heavy products.

The yield of n-butyl 2-chloropropionate is 95.3%.

EXAMPLE 7

The procedure of Example 6 is followed, using n-propyl lactate (660 g, 5 mols) of optical rotation $[\alpha]_D^{20} = -13.16°$ (without a solvent), thionyl chloride (640 g, 5.37 mols) and pyridine (1.3 g).

The n-propyl lactate is run in at 60° C. in the course of 4 hours and this is followed by heating at 75° C. for 1 hour 5 minutes. After cooling under atmospheric pressure, a crude product (831 g) composed mainly of n-propyl chloropropionate is recovered.

Distillation of the crude product obtained (731 g) under a pressure of 12 mm Hg (+69° C.) gives a first fraction (125 g) of optical rotation $[\alpha]_D^{20} = +13.97°$ (without a solvent), which is composed of at least 93% by weight of n-propyl 2-chloropropionate and contains 0.5% by weight of free $SO_2$ and less than 6.5% of thionyl chloride, a second fraction (465 g) of optical rotation $[\alpha]_D^{20} = +14.30°$ (without a solvent), which is composed of at least 99.9% by weight of n-propyl 2-chloropropionate and contains less than 0.1% of free $SO_2$, and a residue (27 g) which is composed of 95.5% by weight of n-propyl 2-chloropropionate and 4.5% of heavy products.

The yield of n-propyl 2-chloropropionate is 95.1%.

EXAMPLE 8

Thionyl chloride (50 g, 0.42 mol), pyridine (4.15 g) and methyl 2-chloropropionate (500 g), prepared beforehand and having an optical rotation $[\alpha]_D^{20} = -24.8°$ (without a solvent), are introduced into a round-bottomed flask equipped with a stirrer, A Vigreux-type condenser and two dropping funnels.

Methyl lactate (832 g, 8 mols), $[\alpha]_D^{20} = +7.48°$ (without a solvent), which contains 1.03% of ethyl lactate as an impurity and 0.61% of other unidentified impurities, is placed in one of the dropping funnels. Thionyl chloride (973 g, 8.18 mols) is placed in the other dropping funnel.

The methyl lactate and the thionyl chloride are simultaneously run into the flask in the course of 4 hours, at 60° C., the respective rates of introduction of the reactants being adjusted so that the amount of thionyl chloride introduced into the flask is always in a molar excess of at least 2.5%, relative to the amount of methyl lactate introduced.

When the introduction is complete, the temperature of the reaction mixture is increased from 60° C. to 75° C. in the course of 5 minutes and this temperature is maintained for 1 hour 30 minutes; a crude product (1,588 g) composed of more than 90% of methyl chloropropionate is obtained. The remainder mainly consists of the excess thionyl chloride and dissolved $SO_2$.

Distillation of the crude product thus obtained (1,588 g) in a 40 cm high packed column, in a partial vacuum of 40 mm Hg which is reduced to 3 mm Hg at the end of the distillation, makes it possible to separate the following three fractions:

First fraction (263 g) consisting of methyl 2-chloropropionate (247.5 g) containing about 1% by weight of ethyl 2-chloropropionate, thionyl chloride (13.1 g), free $SO_2$ (1.3 g) and free HCl (1.0 g).

Second fraction (1,035.4 g), $[\alpha]_D^{20} = -25.06°$ (without a solvent), consisting of a mixture of methyl and ethyl 2-chloropropionate (1,033.6 g) containing about 1% by weight of ethyl 2-chloropropionate, $SO_2$ (0.9 g) and HCl (0.9 g).

Third fraction (129 g), $[\alpha]_D^{20} = -24.59°$ (without a solvent), consisting of methyl 2-chloropropionate (128.9 g) containing about 1% by weight of ethyl 2-chloropropionate, and HCl (0.07 g).

At the bottom of the column, a residue (14 g) composed of pyridine hydrochloride and heavy products is recovered.

After distillation, scrubbing of the column makes it possible to recover methyl 2-chloropropionate (6 g).

The yield of methyl 2-chloropropionate is 94%.

We claim:

1. A process for the preparation of an optically active alkyl 2-chloropropionate of the formula:

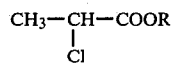

in which R represents an alkyl radical containing from 1 to 5 carbon atoms, by reacting excess thionyl chloride with an optically active alkyl lactate of the formula:

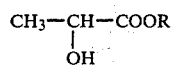

in which R has the same meaning as above, with, in a first step, the formation of the chlorosulphinate of the alkyl lactate, and then, in a second step, the thermal decomposition of the chlorosulphinate of the alkyl lactate, which process comprises, during the first step, gradually bringing the alkyl lactate into contact with the thionyl chloride, in the presence of 0.05-2% by weight of pyridine based on the weight of said alkyl lactate, whilst maintaining, in the reaction mixture, a molar excess of thionyl chloride of at least 2.5%, relative to the amount of alkyl lactate introduced into this mixture, at a temperature which is kept below the decomposition point of the chlorosulphinate of the alkyl lactate during the first step, and, in the second step, heating the reaction mixture resulting from the first step at a temperature which is at least equal to the decomposition point of the chlorosulphinate of the alkyl lactate.

2. A process according to claim 1, wherein, during the first step of the process, the alkyl lactate is gradually run into the reaction mixture containing at least some of the thionyl chloride to be used and at least some of the pyridine to be used.

3. A process according to claim 2, wherein, during the first step of the process, the alkyl lactate and some of the thionyl chloride are simultaneously run into the reaction mixture containing the pyridine and the remainder of the thionyl chloride.

4. A process according to claim 2, wherein, during the first step of the process, the alkyl lactate is run into the reaction mixture containing the pyridine and the thionyl chloride.

5. A process according to either one of claims 3 and 4, wherein the time required to bring all the thionyl chloride into contact with all the alkyl lactate is at least two hours, and, during this time, the temperature of the reaction mixture is kept between 0° and 70° C.

6. A process according to claim 5, wherein the amount of pyridine used is between 0.1% and 1% by weight of the amount of alkyl lactate to be converted, and during the second step of the process, this reaction mixture is heated at a temperature between 60° and 80° C.

7. A process, according to claim 6, for the preparation of an alkyl 2-chloropropionate which predominantly comprises the isomer of the D absolute configuration, wherein the alkyl lactate used as the starting material predominantly comprises the isomer of the L absolute configuration.

8. A process, according to claim 6, for the preparation of an alkyl 2-chloropropionate which predominantly comprises the isomer of the L absolute configuration, wherein the alkyl lactate used as the starting material predominantly comprises the isomer of the D absolute configuration.

9. A process according to claim 1, wherein, during the first step of the process, the temperature is maintained in the range of 15°–65° C.

* * * * *

UNITED STATES PATENT AND TRADEMARK OFFICE
CERTIFICATE OF CORRECTION

PATENT NO. : 4,334,083
DATED : June 8, 1982
INVENTOR(S) : Buathier et al

It is certified that error appears in the above-identified patent and that said Letters Patent are hereby corrected as shown below:

Column 1, line 34, delete "i.e. the letters D and L, will be used systematically). II)" and insert therefor --i.e. the letters D and L, will be used systematically).

The compound of the formula I (or of the formula II)--.

Signed and Sealed this

Third Day of May 1983

[SEAL]

Attest:

Attesting Officer

GERALD J. MOSSINGHOFF
Commissioner of Patents and Trademarks